US008969381B2

(12) United States Patent
Wilson et al.

(10) Patent No.: US 8,969,381 B2
(45) Date of Patent: Mar. 3, 2015

(54) CHEMOKINE CXCR4 RECEPTOR MODULATORS AND USED RELATED THERETO

(75) Inventors: Lawrence J. Wilson, Atlanta, GA (US); John Wiseman, Atlanta, GA (US); Dennis C. Liotta, Atlanta, GA (US); Michael G. Natchus, Alpharetta, CA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/879,809

(22) PCT Filed: Dec. 2, 2011

(86) PCT No.: PCT/US2011/063007
§ 371 (c)(1),
(2), (4) Date: Aug. 14, 2013

(87) PCT Pub. No.: WO2012/075362
PCT Pub. Date: Jun. 7, 2012

(65) Prior Publication Data
US 2013/0324552 A1   Dec. 5, 2013

Related U.S. Application Data

(60) Provisional application No. 61/419,545, filed on Dec. 3, 2010.

(51) Int. Cl.
| *A61K 31/04* | (2006.01) |
| *C07D 215/38* | (2006.01) |
| *C07D 401/12* | (2006.01) |
| *C07D 401/14* | (2006.01) |
| *A61K 31/4709* | (2006.01) |
| *A61K 31/4725* | (2006.01) |
| *A61K 31/496* | (2006.01) |
| *A61K 45/06* | (2006.01) |

(52) U.S. Cl.
CPC .......... *C07D 401/12* (2013.01); *C07D 401/14* (2013.01); *A61K 31/4709* (2013.01); *A61K 31/4725* (2013.01); *A61K 31/496* (2013.01); *A61K 45/06* (2013.01)
USPC ........................................ 514/312; 546/159

(58) Field of Classification Search
USPC .......................................... 546/159; 514/312
See application file for complete search history.

(56) References Cited

U.S. PATENT DOCUMENTS

| 6,429,308 B1 | 8/2002 | Iijima et al. |
| 2004/0209921 A1 | 10/2004 | Bridger |
| 2006/0128750 A1 | 6/2006 | Bridger |
| 2008/0255197 A1 | 10/2008 | Bridger |

FOREIGN PATENT DOCUMENTS

| WO | WO0156591 A1 | 8/2001 |
| WO | WO2006020415 A1 | 2/2006 |
| WO | WO2009121063 A2 | 10/2009 |

OTHER PUBLICATIONS

Westby et al., Emergence of CXCR4—using human immunodeficiency virus type 1 (HIV-1) variants in a minority of HIV-1-infected patients following treatment with the CCR5 antagonist maraviroc is from a pretreatment CXCR4—using virus reservoir, Journal of Virology, 2006, 4909-4920, 80.
Staller et al., Chemokine receptor CXCR4 downregulated by von Hippel—Lindau tumour suppressor pVHL, Nature, 2003, 307-311, 425.
Kang et al., A multigenic program mediating breast cancer metastasis to bone., Cancer Cell, 2003, 537-549, 3.
Muller et al., Involvement of chemokine receptors in breast cancer metastasis, Nature, 2001, 50-56, 410.
Wald et al., Involvement of the CXCL12/CXCR4 pathway in the advanced liver disease that is associated with hepatitis C virus or hepatitis B virus, European Journal of Immunology, 2004, 1164-1174, 34.
Mitra et al., CXCR4 mRNA expression in colon, esophageal and gastric cancers and hepatitis C infected liver, International Journal of Oncology, 1999, 917-925, 14.
Grove, Epidermal Cell Kinetics in Psoriasis, International Journal of Dermatology, 1979, 111, 18.
Ross, The pathogenesis of atherosclerosis: a perspective for the 1990s, Nature, 1993, 801-809, 362.
Harris, Mechanisms of Disease: Rheumatoid Arthritis—Pathophysiology and Implications for Therapy, The New England Journal of Medicine, 1990, 1277-1289, 322.
Crane et al., CXCR4 Receptor Expression on Human Retinal Pigment Epithelial Cells from the Blood-Retina Barrier Leads to Chemokine Secretion and Migration in Response to Stromal Cell-Derived Factor 1α, J. Immunol., 2000, 4372-4378, 165.
Dwinell et al., Chemokine receptor expression by human intestinal epithelial cells, Gastroenterology, 1999, 359-367, 117.
Bressler et al., Preventative Ophthalmology Age-related Macular Degeneration, Ophthalmology, 1995, 1206-1211, 102.
Gupta et al., Chemokine Receptors in Human Endothelial Cells: Functional Expression of CXCR4 and Its Transcriptional Regulation by Inflammatory Cytokines, J. Biol. Chem., 1998, 4282-4287, 273.
Volin et al., Chemokine receptor CXCR4 expression in endothelium, Biochem. Biophys. Res. Commun., 1998, 46, 242.
Murdoch et al., Functional expression of chemokine receptor CXCR4 on human epithelial cells, Immunology, 1999, 36-41, 98.
Alkhatib et al., CC CKR5: A RANTES, MIP-1α, MIP-1β Receptor as a Fusion Cofactor for Macrophage-Tropic HIV-1, Science, 1996, 1955-1988, 272.
Challita-Eid et al., Inhibition of HIV Type 1 Infection with a RANTES-IgG3 Fusion Protein, AIDS Research and Human Retroviruses, 1998, 1617-1624, 14.
Truax et al., Discovery of Tetrahydroisoquinoline-Based CXCR4 Antagonists, ACS Med. Chem. Lett. 2013, 4, 1025-1030.
Reitsema, A Novel Rearrangement of a piperdine ring, Journal of the American Chemical Society, ACS Publications, US, 1949, vol. 71: 2041-2043.

*Primary Examiner* — D M Seaman
(74) *Attorney, Agent, or Firm* — Emory Patent Group

(57) ABSTRACT

The disclosure relates to chemokine CXCR4 receptor modulators and uses related thereto. In certain embodiments, the disclosure relates to pharmaceutical compositions comprising compounds disclosed herein or pharmaceutically acceptable salts or prodrugs thereof. In certain embodiments, the compositions disclosed herein are used for managing CXCR4 related conditions, typically prevention or treatment of viral infections such as HIV or for managing cancer.

13 Claims, No Drawings

CHEMOKINE CXCR4 RECEPTOR MODULATORS AND USED RELATED THERETO

CROSS-REFERENCE TO RELATED APPLICATIONS

This application claims priority to U.S. Provisional Application No. 61/419,545, filed Dec. 3, 2010, the contents of which is incorporated herein in its entirety.

FIELD

The disclosure relates to chemokine CXCR4 receptor modulators and uses related thereto. In certain embodiments, the disclosure relates to pharmaceutical compositions comprising compounds disclosed herein or pharmaceutically acceptable salts or prodrugs thereof. In certain embodiments, the compositions disclosed herein are used for managing CXCR4 related conditions, typically prevention or treatment of viral infections such as HIV or for managing cancer.

BACKGROUND

As of the end of 2007, an estimated 33 million people worldwide were living with HIV/AIDS, and the Centers for Disease Control and Prevention (CDC) estimates that 1,200,000 U.S. residents are living with HIV infection (UNAIDS/WHO AIDS epidemic update, December 2008; The Henry J. Kaiser Family Foundation HIV/AIDS Policy Fact Sheet, July 2007). Although new infections have decreased in recent years, an estimated 2.6 million new HIV infections occurred worldwide during 2007 and approximately 40,000 new HIV infections occur each year in the United States.

HIV entry within the target cells involves a series of molecular events. The three main steps of virus entry within the cell are: (i) attachment of the virus to the subject cells; (ii) interaction of the virus with the co-receptors; (iii) fusion of the virus and subject cell membranes. Considering the complexity of the molecular events involved in viral infection, all three of these steps have been considered for the drug design. The T-lymphocyte cell surface protein CD4 is the primary receptor involved in the interaction with the viral glycoprotein gp120, but a cellular co-receptor is also needed for the successful entry of the virus within the cell. At least two types of such co-receptors have been identified so far, both of which are chemokine receptors, CCR5 and CXCR4. These chemokine receptors are therefore gateways for HIV entry, determinants of viral tropism and sensitivity.

Compounds targeting viral entry have two advantages over those that target the HIV-1 reverse transcriptase or protease enzymes: entry inhibitors do not depend on efficient cellular uptake or intracellular activation processes to exert their biological effects, and they are highly unlikely to show any cross-resistance with protease inhibitors or reverse transcriptase inhibitors. Viral entry has been validated as a clinically effective pathway for targeted intervention by the first fusion inhibitor, enfuvirtide. Other classes of entry inhibitor under development target the initial binding of viral gp120 to CD4 and the interaction of gp120 with cell surface chemokine receptors that serve as co-receptors for HIV entry (CCR5 or CXCR4). Westby et al., Journal of Virology, 2006, 80(10), 4909-4920.

Compounds targeting CXCR4 have been developed primarily for treatment of HIV because CXCR4 is a major co-receptor for T-tropic HIV infection. For example, U.S. Pat. No. 6,429,308 discloses an antisense oligonucleotide to CXCR4 to inhibit the expression of the CXCR4 protein for use as an anti-HIV agent. International patent application publication number WO 2001/56591 describes peptide fragments of viral macrophage inflammatory protein II which are described as selectively preventing CXCR4 signal transduction and co-receptor function in mediating entry of HIV-I. Additional molecular antagonists of chemokine CXCR4 receptor are disclosed in international patent application publication numbers WO 2009/121063 and WO 2006/020415.

Studies have shown that CXCR4 interactions also regulate the migration of metastatic cells. Hypoxia, a reduction in partial oxygen pressure, is a micro-environmental change that occurs in most solid tumors and is a major inducer of tumor angiogenesis and therapeutic resistance. Hypoxia increases CXCR4 levels (Staller, et al. (2003) Nature 425: 307-311). Microarray analysis on a sub-population of cells from a bone metastatic model with elevated metastatic activity showed that one of the genes increased in the metastatic phenotype was CXCR4. Furthermore, over-expression of CXCR4 in isolated cells significantly increased the metastatic activity (Kang, et al. (2003) Cancer Cell 3: 537-549). In samples collected from various breast cancer patients, Muller et al. (Muller, et al. (2001) Nature 410: 50-56) found that CXCR4 expression levels are higher in primary tumors relative to normal mammary gland or epithelial cells. These results suggest that the expression of CXCR4 on cancer cell surfaces may direct the cancer cells to sites that express high levels of SDF-I. Consistent with this hypothesis, SDF-I is highly expressed in the most common destinations of breast cancer metastasis including lymph nodes, lung, liver, and bone marrow. Moreover, CXCR4 antibody treatment has been shown to inhibit metastasis to regional lymph nodes when compared to control isotypes that all metastasized to lymph nodes and lungs (Muller, et al. (2001) Nature 410: 50-56).

In addition to regulating migration of cancer cells, CXCR4-SDF-1 interactions may regulate vascularization necessary for metastasis. Blocking either CXCR4/SDF-1 interaction or the major G-protein of CXCR4/SDF-1 signaling pathway (Gal) inhibits VEGF-dependent neovascularization. These results indicate that SDF-1/CXCR4 controls VEGF signaling systems that are regulators of endothelial cell morphogenesis and angiogenesis. Numerous studies have shown that VEGF and MMPs actively contribute to cancer progression and metastasis. Thus, there is a need to identify CXCR4 antagonists for therapeutic applications in treating or preventing cancer.

SUMMARY

The disclosure relates to chemokine CXCR4 receptor modulators and uses in therapeutic and diagnostic applications. In certain embodiments, the disclosure relates to compounds comprising formula I,

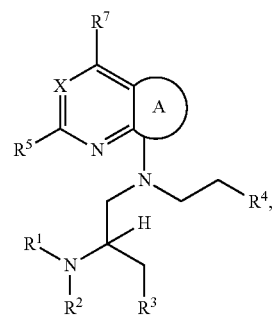

formula I or salts thereof wherein,

A is a carbocyclic or heterocyclic ring, wherein A is optionally substituted with one or more, the same or different, $R^{10}$;

X is C—$R^6$ or N;

$R^1$ is hydrogen or alkyl, wherein $R^1$ is optionally substituted with one or more, the same or different, $R^{10}$;

$R^2$ and $R^3$ together with the atoms they are bonded to form a carbocyclyl or hetercyclyl, wherein the carbocyclyl or heterocyclyl are optionally substituted with one or more, the same or different, $R^{10}$;

$R^4$ is hydrogen, alkyl, halogen, cyano, hydroxy, amino, mercapto, formyl, carboxy, carbamoyl, alkoxy, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$;

$R^5$, $R^6$ and $R^7$ are each individually and independently hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to isolated compositions comprising compounds disclosed herein in substantially pure form.

In certain embodiments, the disclosure relates to a pharmaceutical comprising a compound as described herein including salts and prodrugs thereof and a pharmaceutically acceptable excipient, diluent, or carrier.

In certain embodiments, the pharmaceutical composition comprises compounds in greater than 60%, 70%, 80%, 90%, 95%, 98%, diastereomeric or enantiomeric excess.

In certain embodiments, the disclosure relates to uses of compounds disclosed herein in the production of a medicament for the treatment of CXCR4 related conditions, such as, viral infections, abnormal cellular proliferation, retinal degeneration, inflammatory diseases, or as an immunostimulant or immunosuppressant.

In certain embodiments, the disclosure relates to pharmaceutical compositions comprising a compound as described herein and another active ingredient such as an antiviral agent or chemotherapeutic agent.

In certain embodiments, the disclosure relates to administering a CXCR4 antagonist disclosed herein in combination with a CCR5 antagonist such as maraviroc (selzentry) or vicriviroc.

In certain embodiments, the disclosure relates to methods of treating or preventing an viral infection comprising administering pharmaceutical composition comprising a compound as described herein optionally in combination with another active ingredient to a subject in need thereof. In further embodiments, the subject is at risk of, exhibiting symptoms of, or diagnosed with a viral infection.

In certain embodiments, the disclosure relates to uses of a compound as described herein in the production of a medicament for the treatment of a viral infection. In a typically embodiments, the viral infection is an HIV infection.

In certain embodiments, the disclosure relates to methods of treating or preventing cancer comprising administering pharmaceutical composition comprising a compound as described herein optionally in combination with another active ingredient to a subject in need thereof. In further embodiments, the subject is at risk of, exhibiting symptoms of, or diagnosed with cancer.

DETAILED DESCRIPTION

Terms

When describing the compounds for use in the disclosure, the terms used are to be construed in accordance with the following definitions, unless a context dictates otherwise.

As used herein, "alkyl" means a noncyclic straight chain or branched, unsaturated or saturated hydrocarbon such as those containing from 1 to 10 carbon atoms, typically 1 to 4 otherwise designated $C_{1-4}$alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH3).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. "Alkylamino" refers an alkyl group as defined above attached through an amino bridge. An example of an alkylamino is methylamino, (i.e., —NH—CH3).

"Aminoalkyl" refers to an amino group attached through an alkyl bridge as defined above (i.e., NH$_2$-alkyl-).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)2alkyl) such as mesyl and the like, and "arylsulfonyl" refers to an aryl attached through a sulfonyl bridge (i.e., —S(=O)2aryl).

"Alkylsulfamoyl" refers to an alkyl as defined above attached through a sulfamoyl bridge (i.e., —NHS(=O)2alkyl), and an "Arylsulfamoyl" refers to an alkyl attached through a sulfamoyl bridge (i.e., —NHS(=O)2aryl).

"Alkylsulfinyl" refers to an alkyl as defined above attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

CXCR4 Antagonist

In certain embodiments, the disclosure relates to pharmaceutical compositions comprising compounds or formula I,

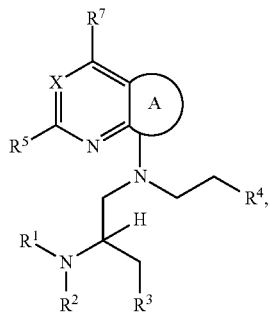

formula I or salts thereof wherein,

A is a carbocyclyl or heterocyclyl, wherein A is optionally substituted with one or more, the same or different, $R^{10}$;

X is C—$R^6$ or N;

$R^1$ is hydrogen, $C_{1-4}$alkyl, wherein $R^1$ is optionally substituted with one or more, the same or different, $R^{10}$;

$R^2$ and $R^3$ together with the atoms they are bonded to form a carbocyclyl or heterocyclyl, wherein the carbocyclyl or heterocyclyl are optionally substituted with one or more, the same or different, $R^{10}$;

$R^4$ is hydrogen, alkyl, halogen, cyano, hydroxy, amino, mercapto, formyl, carboxy, carbamoyl, alkoxy, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$;

$R^5$, $R^6$ and $R^7$ are each individually and independently hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, formula I is formula IA,

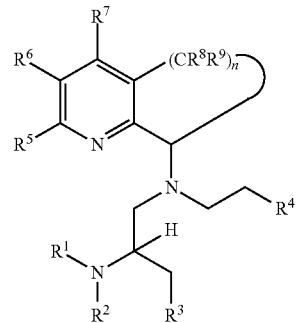

formula IA wherein, n is 2, 3, or 4; and $R^8$ and $R^9$ are each individually and independently hydrogen, halogen, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, formula I is formula IB

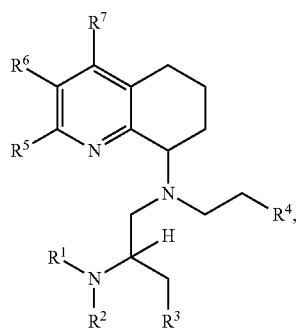

wherein substituents are as defined herein

In certain embodiments, formula I is formula IC

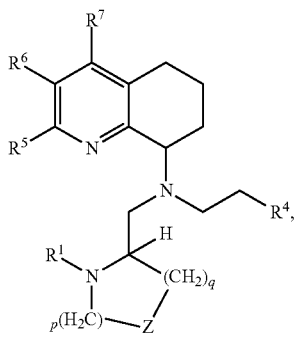

wherein, Z is the bridging group —(CH$_2$)$_m$—NR$^{13}$—, —(CH$_2$)$_m$—CHR$^{13}$—, or

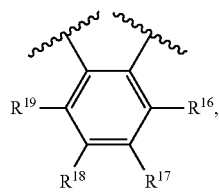

m is 0, 1, or 2;
p is 0, 1, or 2;
q is 0, 1, or 2;
R$^{13}$ is hydrogen alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{13}$ is optionally substituted with one or more, the same or different, R$^{14}$;
R$^{14}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{14}$ is optionally substituted with one or more, the same or different, R$^{15}$; and
R$^{15}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and
R$^{16}$, R$^{17}$, R$^{18}$ and R$^{19}$ are each individually and independently hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, R$^1$ is hydrogen or alkyl.
In certain embodiments, R$^4$ is —CH$_2$CH$_2$NH$_2$ optionally substituted with one or more the same or different R$^{10}$.
In certain embodiments, R$^5$, R$^6$, and R$^7$ are hydrogen, halogen, alkyl, or alkoxy.
In certain embodiments, R$^{13}$ is alkyl, alkoxy, phenyl, benzyl, benyloxy, benzoyl, optionally substituted with one or more, the same or different, R$^{14}$;
In certain embodiments formula I is formula ID, IE, IF, IG, IH, II, IJ, or IK, formula ID formula IE formula IF formula IG -continued formula IH

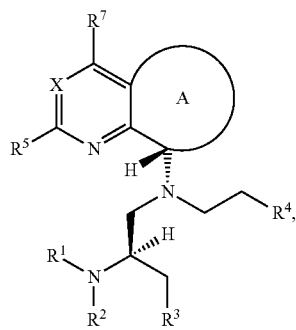

formula II

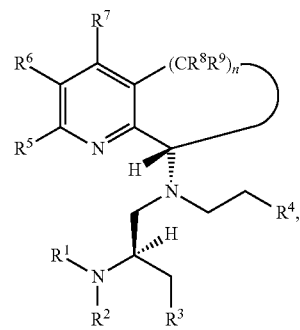

formula IJ

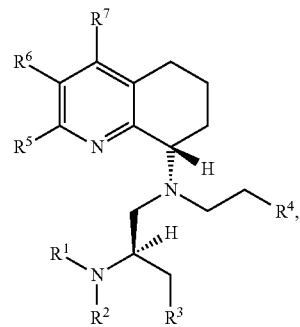

formula IK

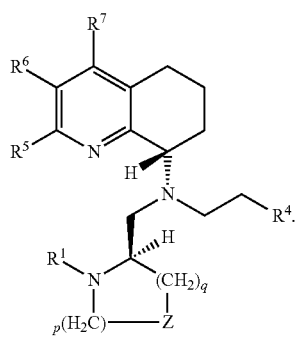

In certain embodiments, the compound is of the following formula IIA or IIB:

IIA

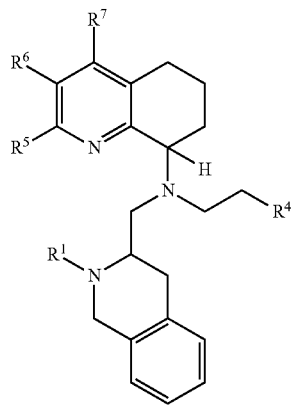

IIB

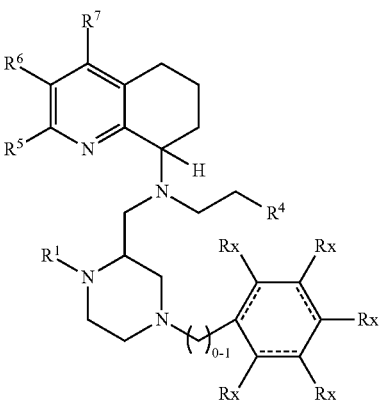

wherein $R^1$, $R^4$, $R^5$, $R^6$ and $R^7$ are as described above, and each Rx is either absent or is independently selected from hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In particular subembodiments, the following compounds are provided

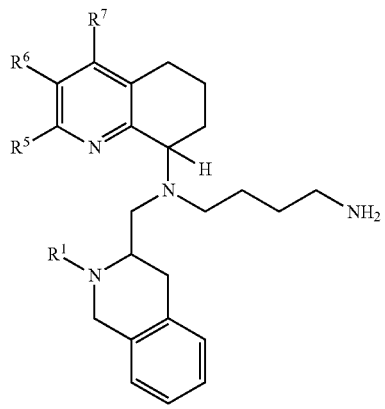

wherein the substituents are as described herein.

In further subembodiments, the following compounds are provided

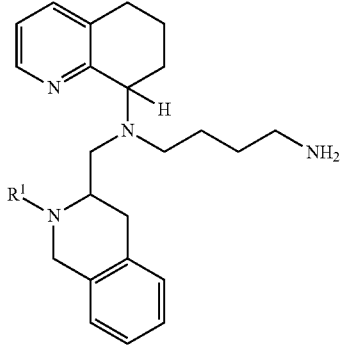

wherein the substituents are as described herein.

In other particular embodiments, compounds are provided

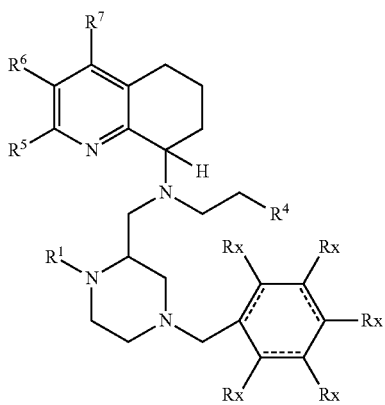

wherein the substituents are as described herein.

In further subembodiments, compounds are provided

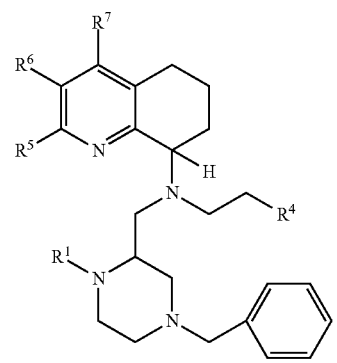

wherein the substituents are as described herein.

In further subembodiments, compounds are provided

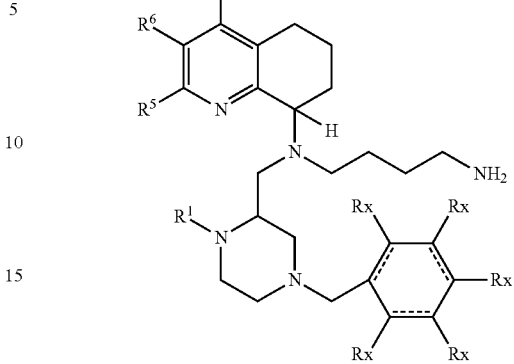

wherein the substituents are as described herein.

In further subembodiments, compounds are provided

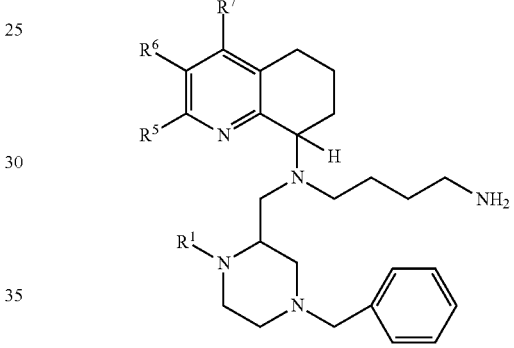

wherein the substituents are as described herein.

In further subembodiments, compounds are provided

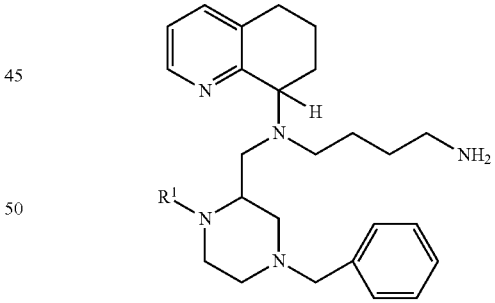

wherein the substituents are as described herein.

In certain of the above embodiments, $R^1$ is hydrogen.

In certain embodiments, compounds of formula I are substituted or unsubstituted compounds of $N^1$—(((S)-1,2,3,4-tetrahydroisoquinolin-3-yl)methyl)-$N^1$—((S)-5,6,7,8-tetrahydroquinolin-8-yl)butane-1,4-diamine;

$N^1$—(((R)-1,2,3,4-tetrahydroisoquinolin-3-yl)methyl)-$N^1$—((S)-5,6,7,8-tetrahydroquinolin-8-yl)butane-1,4-diamine;

$N^1$—(((S)-4-benzylpiperazin-2-yl)methyl)-$N^1$—((S)-5,6,7,8-tetrahydroquinolin-8-yl)butane-1,4-diamine;

$N^1$—(((R)-4-benzylpiperazin-2-yl)methyl)-$N^1$—((S)-5,6,7,8-tetrahydroquinolin-8-yl)butane-1,4-diamine;

((R)-3-(((4-aminobutyl)((S)-5,6,7,8-tetrahydroquinolin-8-yl)amino)methyl)piperazin-1-yl)(phenyl)methanone;

((S)-3-(((4-aminobutyl)((S)-5,6,7,8-tetrahydroquinolin-8-yl)amino)methyl)piperazin-1-yl)(phenyl)methanone;

$N^1$—(((R)-4-phenylpiperazin-2-yl)methyl)-$N^1$—((S)-5,6,7,8-tetrahydroquinolin-8-yl)butane-1,4-diamine;

$N^1$—(((S)-4-phenylpiperazin-2-yl)methyl)-$N^1$—((S)-5,6,7,8-tetrahydroquinolin-8-yl)butane-1,4-diamine;

$N^1$-(((2S)-4-phenylpiperidin-2-yl)methyl)-$N^1$—((S)-5,6,7,8-tetrahydroquinolin-8-yl)butane-1,4-diamine;

$N^1$-(((2R)-4-phenylpiperidin-2-yl)methyl)-$N^1$—((S)-5,6,7,8-tetrahydroquinolin-8-yl)butane-1,4-diamine;

(2S)-benzyl 4-(4-aminobutoxy)-2-(((4-aminobutyl)((S)-5,6,7,8-tetrahydroquinolin-8-yl)amino)methyl)pyrrolidine-1-carboxylate;

(2R)-benzyl 4-(4-aminobutoxy)-2-(((4-aminobutyl)((S)-5,6,7,8-tetrahydroquinolin-8-yl)amino)methyl)pyrrolidine-1-carboxylate;

$N^1$-(((2S)-4-(benzyloxy)pyrrolidin-2-yl)methyl)-$N^1$—((S)-5,6,7,8-tetrahydroquinolin-8-yl)butane-1,4-diamine;

$N^1$-(((2S)-4-(benzyloxy)pyrrolidin-2-yl)methyl)-$N^1$—((S)-5,6,7,8-tetrahydroquinolin-8-yl)butane-1,4-diamine;

$N^1$-(((2S)-4-phenylpyrrolidin-2-yl)methyl)-$N^1$—((S)-5,6,7,8-tetrahydroquinolin-8-yl)butane-1,4-diamine;

$N^1$-(((2R)-4-phenylpyrrolidin-2-yl)methyl)-$N^1$—((S)-5,6,7,8-tetrahydroquinolin-8-yl)butane-1,4-diamine;

$N^1$—((S)-isoindolin-1-ylmethyl)-$N^1$—((S)-5,6,7,8-tetrahydroquinolin-8-yl)butane-1,4-diamine;

$N^1$—((R)-isoindolin-1-ylmethyl)-$N^1$—((S)-5,6,7,8-tetrahydroquinolin-8-yl)butane-1,4-diamine;

$N^1$—(((S)-1,2,3,4-tetrahydroisoquinolin-1-yl)methyl)-$N^1$—((S)-5,6,7,8-tetrahydroquinolin-8-yl)butane-1,4-diamine;

$N^1$—(((R)-1,2,3,4-tetrahydroisoquinolin-1-yl)methyl)-$N^1$—((S)-5,6,7,8-tetrahydroquinolin-8-yl)butane-1,4-diamine;

$N^1$—(((S)-1,2,3,4-tetrahydroquinolin-2-yl)methyl)-$N^1$—((S)-5,6,7,8-tetrahydroquinolin-8-yl)butane-1,4-diamine; and $N^1$—(((R)-1,2,3,4-tetrahydroquinolin-2-yl)methyl)-$N^1$—((S)-5,6,7,8-tetrahydroquinolin-8-yl)butane-1,4-diamine or salts or prodrugs thereof.

Methods of Use

In certain embodiments, the compounds described herein are useful for the treatment of viral infections where the virus utilized CXCR4 to infect cells.

In one embodiment, the disclosure relates to a method of treating or preventing HIV infection or reduction of symptoms associated with AIDS is provided including administering a compound disclosed herein to a subject. In certain embodiments, the compound can be provided to a subject before treatment of infection with another compound. In a separate embodiment, the compound is provided to a patient that has been treated for HIV infection to reduce the likelihood of recurrence, or reduce mortality associated with AIDS related symptoms. In another embodiment, the compound is administered to a subject at high risk of suffering from HIV infections.

HIV is a lentivirus (a member of the retrovirus family) that causes acquired immunodeficiency syndrome (AIDS). Lentiviruses are transmitted as single-stranded, positive-sense, enveloped RNA viruses. Upon entry of the target cell, the viral RNA genome is converted to double-stranded DNA by a virally encoded reverse transcriptase. This viral DNA is then integrated into the cellular DNA by a virally encoded integrase, along with host cellular co-factors. There are two species of HIV. HIV-1 is sometimes termed LAV or HTLV-III.

HIV infects primarily vital cells in the human immune system such as helper T cells (CD4+ T cells), macrophages, and dendritic cells. HIV infection leads to low levels of CD4+ T cells. When CD4+ T cell numbers decline below a critical level, cell-mediated immunity is lost, and the body becomes progressively more susceptible to other viral or bacterial infections. Subjects with HIV typically develop malignancies associated with the progressive failure of the immune system.

The viral envelope is composed of two layers of phospholipids taken from the membrane of a human cell when a newly formed virus particle buds from the cell. Embedded in the viral envelope are proteins from the host cell and a HIV protein known as Env. Env contains glycoproteins gp120, and gp41. The RNA genome consists of at structural landmarks (LTR, TAR, RRE, PE, SLIP, CRS, and INS) and nine genes (gag, pol, and env, tat, rev, nef, vif, vpr, vpu, and sometimes a tenth tev, which is a fusion of tat env and rev) encoding 19 proteins. Three of these genes, gag, pol, and env, contain information needed to make the structural proteins for new virus particles. HIV-1 diagnosis is typically done with antibodies in an ELISA, Western blot, or immunoaffinity assays or by nucleic acid testing (e.g., viral RNA or DNA amplification).

Subjects, including humans suffering from, or at risk for, HIV infection can be treated by administering an effective amount of the active compound or a pharmaceutically acceptable prodrug or salt thereof in the presence of a pharmaceutically acceptable carrier or diluent.

The administration can be prophylactically for the prevention of HIV infection or reduction of symptoms associated with AIDS. The active materials can be administered by any appropriate route, for example, orally, parenterally, intravenously, intradermally, subcutaneously, or topically, in liquid or solid form. However, the compounds are particularly suited to oral delivery.

In a separate embodiment, a method for the treatment or prevention of HIV infection or reduction of symptoms associated with AIDS by administering a compound of the present disclosure, or a pharmaceutically acceptable salt, solvate, prodrug, or ester thereof to a subject in need of treatment is provided. The compounds of the disclosure, or a pharmaceutically acceptable salt, solvate, prodrug, or ester thereof can be administered to a subject in need thereof to reduce the severity of AIDS related disorders. In one embodiment of the disclosure, the subject is a human.

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald et al., (2004) European Journal of Immunology. 34(4): 1164-1174). High levels of CXCR4 and TGFβ have been detected in liver samples obtained from patients infected with HCV. (Mitra et al., (1999) Int. J. Oncol. 14: 917-925). In vitro, TGF-β has been shown to up-regulate the expression of CXCR4 on T cells and to increase their migration. The CD69/TGFβ/CXCR4 pathway may be involved in the retention of recently activated lymphocytes in the liver (Wald et al., European Journal of Immunology, 2004; 34(4): 1164-1174).

In another embodiment, the disclosure relates to a method of treating symptoms associated with other infections associated with chemokine receptor activation, for example, liver diseases associated with flavivirus or pestivirus infection, and in particular, HCV or HBV, by contacting a cell with a compound of the present disclosure, or a pharmaceutically acceptable salt, solvate, prodrug, or ester thereof. The cell can be in a subject animal, in particular in a human.

The compounds can be used to treat disorders of abnormal cell proliferation generally, examples of which include, but are not limited to, types of cancers and proliferative disorders listed below. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. Nature, 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr. (1990) The New England Journal of Medicine, 322:1277-1289), and to be caused by auto-antibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of cancers or proliferative disorders which can be the primary tumor that is treated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

In certain embodiments, the subject is diagnosed with acute childhood lymphoblastic leukemia; acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalanic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female Breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lympho proliferative disorders, macroglobulinemia, male breast cancer, malignant mesothelioma, malignant thymoma, medulloblastomia, melanoma, mesothelioma, metastatie occult primary squamous neck cancer, metastatie primary squamous neck cancer, metastatie squamous neck cancer, multiple myeloma, multiple myeloma/plasma cell neoplasm, myelodysplasia syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatie squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid, cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small Intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethial cancer, uterine cancer, uterine sarcoma, vaginal cancer, visual pathway and hypothalamic glioma, vulvar cancer, Waldenstrom's macroglobulinemia, Wilm's tumor, and any other hyperproliferative disease located in an organ system listed above.

In certain embodiments, the compound disclosed herein can be used to treat or prevent hyperplastic disorders including, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblasts, promyelocyte, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and, carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, the disclosure relates to a method for the treatment of, prevention of, or reduced severity of, age-related macular degeneration (ARMD) and other pathogenic states involving macular retinal pigment epithelial (RPE) cells by administering at least one compound described herein to a subject in need thereof.

CXCR4 plays a role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) J. Immunol. 165: 4372-4278). CXCR4 receptor expression on human retinal pigment epithelial cells from the blood-retina barrier leads to chemokine secretion and migration in response to stromal cell-derived factor Ia. J. Immunol. 200; 165: 4372-4278). The level of CXCR4 mRNA expression increases upon stimulation with IL-1β or TNFα (Dwinell, et al. (1999) Gastroenterology. 117: 359-367). RPE cells also migrated in response to SDF-1α indicating that SDF-1α/CXCR4 interactions may modulate the affects of chronic inflammation and subretinal neovascularization at the RPE site of the blood-retina barrier. (Crane U, Wallace C A, McKillop-Smith S, Forrester J V. CXCR4 receptor expression on human retinal pigment epithelial cells from the blood-retina barrier leads to chemokine secretion and migration in response to stromal cell-derived factor Ia. J. Immunol. 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) Ophthalmology. 1995; 102: 1206-1211).

In a separate embodiment, a method for the treatment of, prevention of, or reduced severity of inflammatory disease states, neovascularization, and wound healing including administering at least one compound described herein to a subject in need thereof. Vascular endothelial cells express a multitude of chemokine receptors, with CXCR4 being particularly prominent (Gupta, et al. (1998) J Biol Chem. 273: 4282; Volin, et al. (1998) Biochem Biophys Res Commnun. 242: 46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number of epithelial cell lines derived from various other tissues. (Murdoch, et al. (1998) Immunology. 98(1): 36-41). Unlike with endothelial cells, CXCR4 is the only chemokine receptor expressed on epithelial cells. The receptor may have a functional role in epithelial pathology. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium.

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

In a particular embodiment, the compounds of the disclosure can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

In one embodiment, compounds, compositions and methods of treatment of respiratory disorders comprising administering a compound as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the compounds of the disclosure are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the disclosure is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the disclosure is directed to methods of treating animal subjects, in particular, veterinary and human patients, who are defective in white blood cell (WBQ 8 count, or who would benefit from elevation of WBC levels using the compounds disclosed herein. Moreover, the disclosure is directed to methods of effecting regeneration of cardiac tissue in a subject in need of such regeneration using the disclosed compounds.

The compounds of the disclosure may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round disclosure thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the disclosure targets a broad spectrum of conditions characterized by a deficiency in white blood cell count, or which would benefit from elevation of said WBC count.

Combination Therapies

In certain embodiments, the disclosure relates to pharmaceutical compositions comprising CXCR4 modulators disclosed herein with another active ingredient.

In certain embodiments, the disclosure relates to administering chemokine CXCR4 receptor modulators disclosed herein in combination with natural ligands of CCR5 and CXCR4. The natural ligands for the chemokine receptors CCR5 (RANTES, MIP-1α, and MIP-1β) and CXCR4 (SDF-1) can act as potent inhibitors of infection by the human immunodeficiency virus type 1 (HIV-1) at the level of viral entry. Unlike antibody-mediated inhibition, chemokine-mediated inhibition is broadly effective. Different HIV-1 strains can utilize the same co-receptor(s) for viral entry and, therefore, can be blocked by the same chemokine(s). HIV-1 strains that are highly resistant to neutralization by V3-specific antibodies are sensitive to inhibition by chemokines Therefore, the use of chemokine-modulators constitutes a therapeutic approach to prevent infection by HIV-1. Alkhatib et al., Science. 1996, 272: 1955-1988 and Challita-Eid et al., AIDS Research and Human Retroviruses, 1998, 14(18): 1617-1624.

In some embodiments, the disclosure relates to treating a viral infection by administering a CXCR4 modulator in combination with another, second antiviral agent. In specific embodiments, the compounds described herein are administered in combination or alternation with at least one compound that inhibits HIV entry into a cell through a mechanism not dependent on CXCR4, and in particular embodiments, are administered in combination or alternation with a compound that inhibits CCR5, gp120, gp41 or CD4 binding or activity. In some embodiments, such a compound is at least one of Maraviroc (Celsentri) or Enfuvirtide (Fuzeon). In yet further embodiments such compound is selected from TNX-355, PRO 250, BMS-488043, a theaflavin, Vicriviroc, Gruffithsin, DCM205, ESN196, TBR220, TMB355, Nifeviroc, BMS663068, CYT107, Sifuvirtide, AMD070, PF232798, SP01A.

In further embodiments, the subject is co-administered with abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine.

HIV is typically treated with a combination of antiviral agent, e.g., two nucleoside-analogue reverse transcription inhibitors and one non-nucleoside-analogue reverse transcription inhibitor or protease inhibitor. The three drug combination is commonly known as a triple cocktail. In certain embodiments, the disclosure relates to treating a subject diagnosed with HIV by administering a chemokine CXCR4 receptor modulator disclosed herein in combination with two nucleoside-analogue reverse transcription inhibitors and/or one non-nucleoside-analogue reverse transcription inhibitor or protease inhibitor.

In certain embodiments, the disclosure relates to treating a subject by administering a chemokine CXCR4 receptor modulator disclosed herein, emtricitabine, tenofovir, and efavirenz. In certain embodiments, the disclosure relates to treating a subject by administering a chemokine CXCR4 receptor modulator disclosed herein, emtricitabine, tenofovir and raltegravir. In certain embodiments, the disclosure relates to treating a subject by administering a chemokine CXCR4 receptor modulator disclosed herein, emtricitabine, tenofovir, ritonavir and darunavir. In certain embodiments, the disclosure relates to treating a subject by administering a chemokine CXCR4 receptor modulator disclosed herein, emtricitabine, tenofovir, ritonavir and atazanavir.

In certain embodiments, the disclosure relates to administering a CXCR4 antagonist disclosed herein in combination with a CCR5 antagonist such as maraviroc (selzentry) or vicriviroc.

Banana lectin (BanLec or BanLec-1) is one of the predominant proteins in the pulp of ripe bananas and has binding specificity for mannose and mannose-containing oligosaccharides. BanLec binds to the HIV-1 envelope protein gp120. In certain embodiments, the disclosure relates to treating viral infections, such as HIV, by administering a chemokine CXCR4 receptor modulator disclosed herein in combination with a banana lectin.

The cancer treatment may be applied as a sole therapy or may involve, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778; U.S. Pat. No. 6,369,086; U.S. Pat. No. 6,369,087; and U.S. Pat. No. 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

The additional active agent(s) can be formulated for immediate release, controlled release, or combinations thereof.

EXPERIMENTAL

Methods:

Generally, compounds can be synthesized according to Scheme I below. Three series, the proline series, the piperazine series, and the tetrahydroquinoline series can be synthesized using this scheme. A series of amino acid building blocks are subject to a series of reductive aminations to connect the side chains, with S-tetrahydroquinoline and butyl amine precursors synthesized according to existing methods.

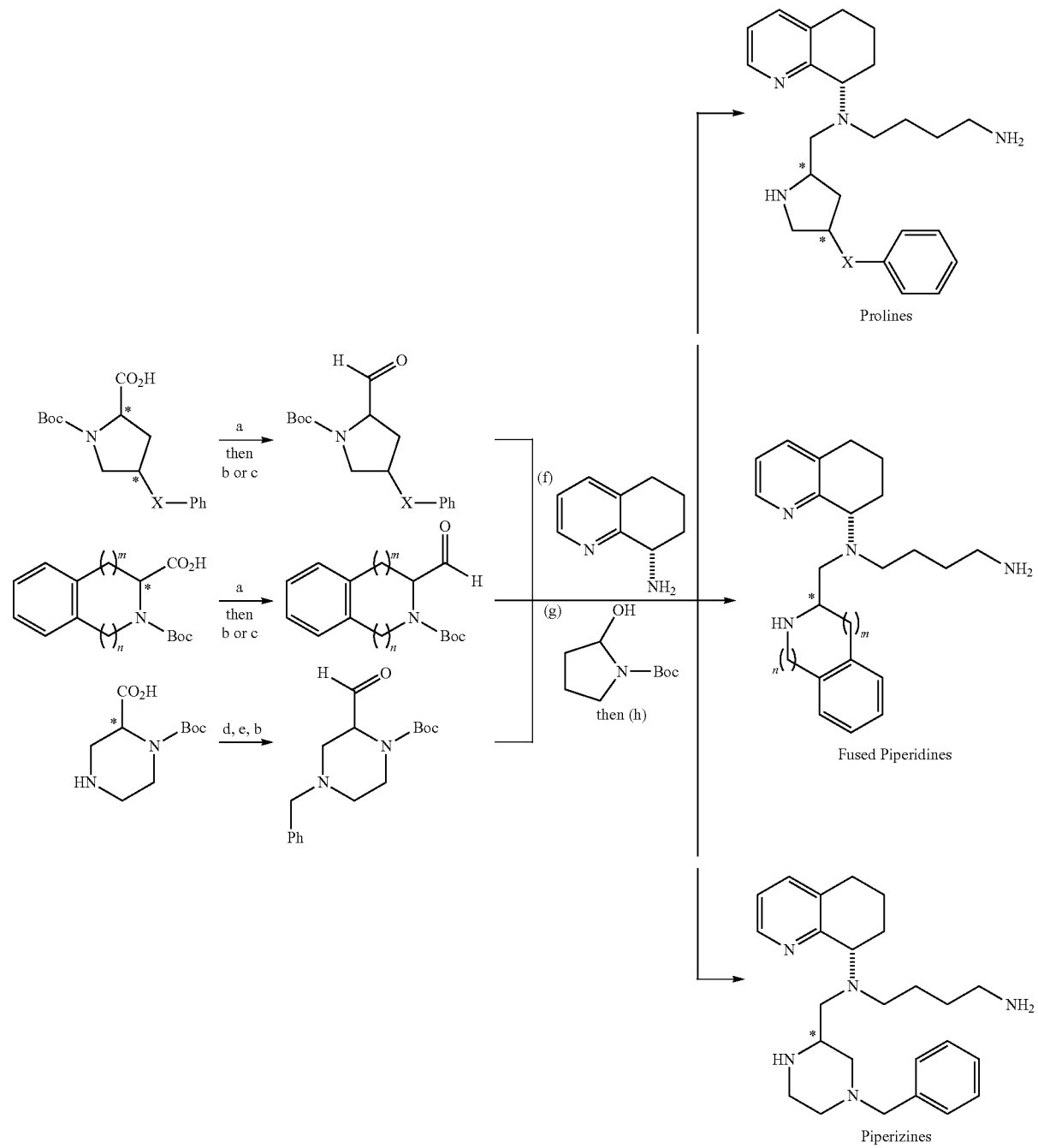

Scheme 1. General scheme for CXCR4 Antagonist Synthesis.

Reagents: (a) $BH_3$—$Me_2S$, THF; (b) Dess-MartinPeriodinane, DCM; (c) $(COCl)_2$, DMSO, DCM, $NEt_3$; (d) $PhCH_2Br$, $K_2CO_3$, DMF; (e) $NaBH_4$, $CaCl_2$, EtOH/THF; (f) $NaBH(OAc)_3$, 1,2-DCE; (g) $NaBH(OAc)_3$, AcOH, DCM; (h) TFA, DCM.

Example 1

[N¹—(((S)-1,2,3,4-tetrahydroisoquinolin-3-yl)methyl)-N¹—((S)-5,6,7,8-tetrahydroquinolin-8-yl)butane-1,4-diamine] and Example 2 [N¹—(((R)-1,2,3,4-tetrahydroisoquinolin-3-yl)methyl)-N¹—((S)-5,6,7,8-tetrahydroquinolin-8-yl)butane-1,4-diamine]

Synthesis of these examples was according to the scheme (Scheme A) provided herein.

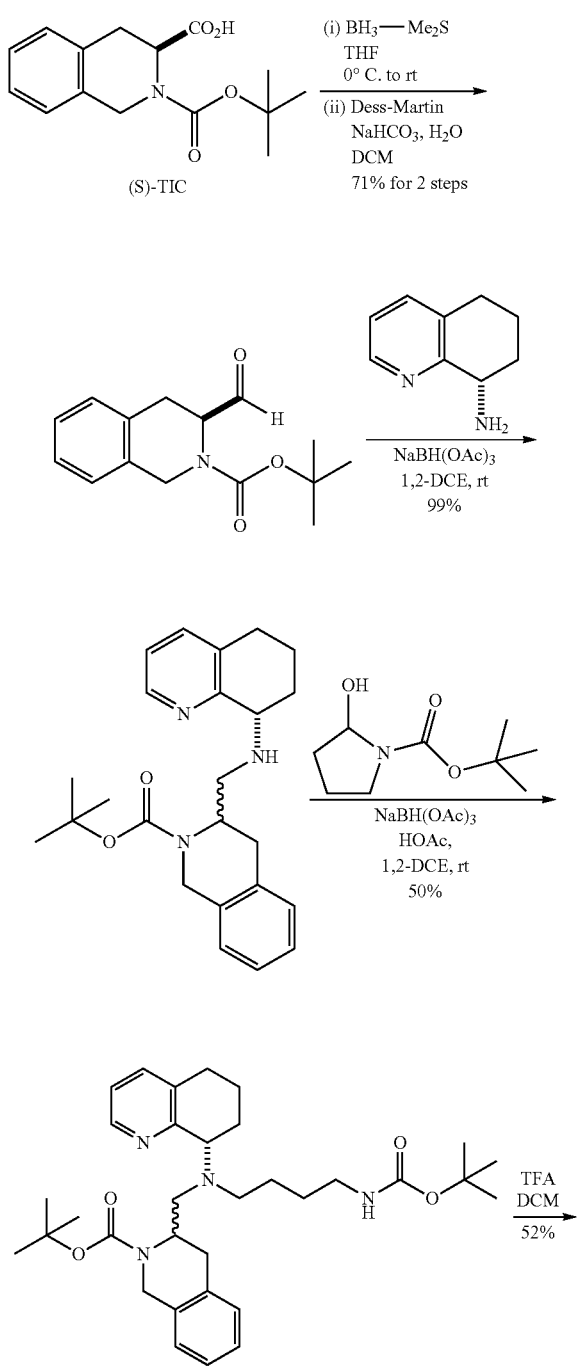

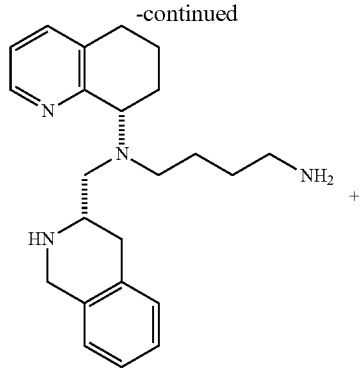

Example 1

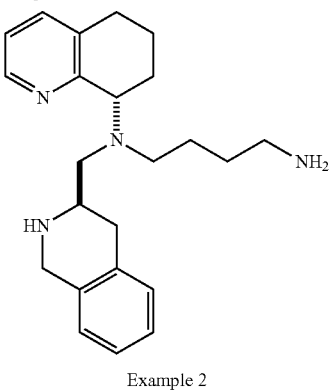

Example 2

Physical Data. Example 2: HPLC retention time=5.7 minutes; MS: 365 (M+H⁺). Example 1: HPLC retention time=6.0 minutes; MS: 365 (M+H⁻).

Procedures for the compounds prepared in Scheme A.

Step (i). Preparation of (S)-tert-butyl 3-(hydroxymethyl)-3,4-dihydroisoquinoline-2(1H)-carboxylate. To 505 mg of (S)-2-(tert-butoxycarbonyl)-1,2,3,4-tetrahydroisoquinoline-3-carboxylic acid (1.82 mmoles) dissolved in 10 mL of tetrahydrofuran at 0° C. was added 3.5 mL of a solution of BH₃—SMe₂ in tetrahydrofuran (2M, 7 mmoles) over a 10 minute period. The reaction was stirred overnight gradually warming to room temperature. The mixture was quenched with methanol, and then a 1N NaOH(aq.) solution was added. The reaction was extracted with ethyl ether and washed with 1N NaOH(aq.) and NaCl(aq.) solutions. The aqueous layers were extracted a second time, and the organic layers were combined and dried over magnesium sulfate. Filtration and solvent removal gave 475 mg of a pale yellow oil.

Step (ii). Preparation of (S)-tert-butyl 3-formyl-3,4-dihydroisoquinoline-2(1H)-carboxylate. The crude material from step (i) was dissolved in 20 mL of dichloromethane. Next 1.5 g of Dess-Martin periodinane and 1 g of NaHCO₃(s) were added, along with 10 drops of H₂O. The reaction was stirred overnight at room temperature. The reaction was filtered over celite with additional dichloromethane. The solvent was removed and the residue diluted with ethyl ether. The organic layer was washed with Na₂S₂O₅(aq.) and Na₂CO₃(aq.) solutions. The aqueous layers were extracted a second time and the organic layers were combined and dried over Na₂SO₄(s). Filtration and solvent removal followed by column chromatography (3:1-hexanes:ethyl acetate) gave 408 mg of pale yellow oil after solvent removal.

Step (iii). Preparation of (S)-tert-butyl 3-((5,6,7,8-tetrahydroquinolin-8-ylamino)methyl)-3,4-dihydroisoquinoline-2(1H)-carboxylate. To a solution of 348 mg of (S)-tert-butyl 3-formyl-3,4-dihydroisoquinoline-2(1H)-carboxylate (1.47 mmoles) and 435 mg of (S)-5,6,7,8-tetrahydroquinolin-8-amine in 10 mL of 1,2-dichloroethane was added 410 mg of NaBH(OAc)$_3$. The reaction was stirred at room temperature overnight. The reaction was extracted with dichloromethane and washed with Na$_2$CO$_3$(aq.). The organics were separated and dried over Na$_2$SO$_4$(s). Filtration, solvent removal and column chromatography (dichloromethane:methanol—90:10) gave 578 mg of a brown viscous oil.

Step (iv). Preparation of (S)-tert-butyl 3-(((4-(tert-butoxycarbonylamino)butyl)(5,6,7,8-tetrahydroquinolin-8-yl)amino)methyl)-3,4-dihydroisoquinoline-2(1H)-carboxylate. To a solution of 578 mg of (S)-tert-butyl 3-((5,6,7,8-tetrahydroquinolin-8-ylamino)methyl)-3,4-dihydroisoquinoline-2(1H)-carboxylate and 394 mg of tert-butyl 2-hydroxypyrrolidine-1-carboxylate in 10 mL of 1,2-dichloroethane was added 0.1 mL of glacial acetic acid and 640 mg NaBH(OAc)$_3$. The reaction was stirred at room temperature for 20 hours. The reaction was extracted with dichloromethane and washed with Na$_2$CO$_3$(aq.). The organic layers were dried over Na$_2$SO$_4$(s). Filtration, solvent removal, and column chromatography (hexanes/ethyl acetate gradient) gave 419 mg of a brown viscous oil.

Step (v). Preparation of Example 1 [N$^1$—(((S)-1,2,3,4-tetrahydroisoquinolin-3-yl)methyl)-N$^1$—((S)-5,6,7,8-tetrahydroquinolin-8-yl)butane-1,4-diamine] and example 2 [N$^1$—(((R)-1,2,3,4-tetrahydroisoquinolin-3-yl)methyl)-N$^1$—((S)-5,6,7,8-tetrahydroquinolin-8-yl)butane-1,4-diamine]. To a solution of 419 mg of (S)-tert-butyl 3-(((4-(tert-butoxycarbonylamino)butyl)(5,6,7,8-tetrahydroquinolin-8-yl)amino)methyl)-3,4-dihydroisoquinoline-2(1H)-carboxylate dissolved in 5 mL of dichloromethane was added 2 mL of trifluoroacetic acid. The solution was stirred at room temperature overnight. The reaction was quenched with NaOH(aq.) solution and extracted with dichloromethane. The organic layers were separated and dried over Na$_2$SO$_4$(s). Filtration and solvent removal followed by column chromatography (dichloromethane:methanol:NH$_4$OH—80:20:2) gave 52 mg of Example 2 (HPLC retention time=5.7 minutes; MS: 365 (M+H$^+$)), and 88 mg of Example 1 (HPLC retention time=6.0 minutes; MS: 365 (M+H$^+$)).

Following similar procedures substituting in the corresponding aldehyde, the following compounds were synthesized:

| Compound | Mass Spectroscopy Data |
|---|---|
| 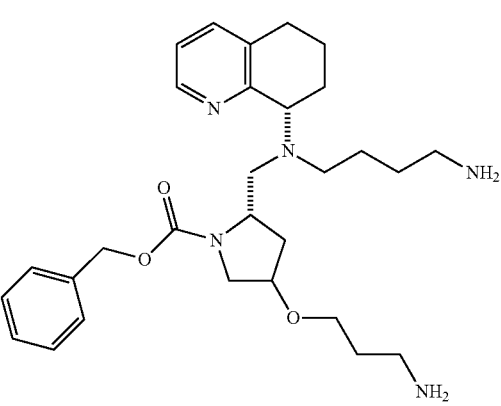 | 510 (M + H$^+$) |
| 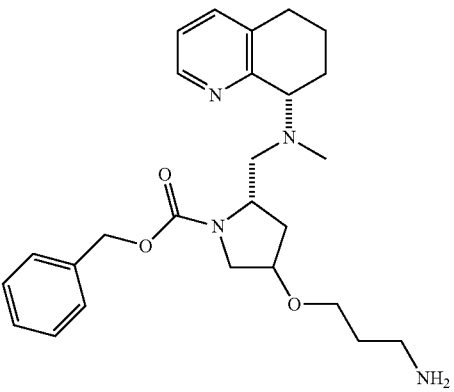 | 453 (M + H$^+$) |

-continued
| Compound | Mass Spectroscopy Data |
|---|---|
| 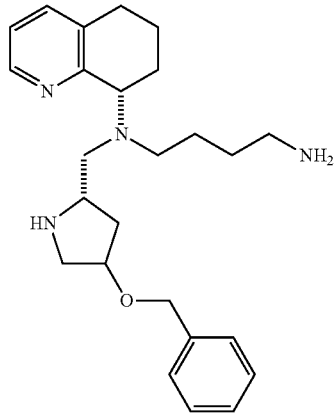 | 409 (M + H⁺) |
| 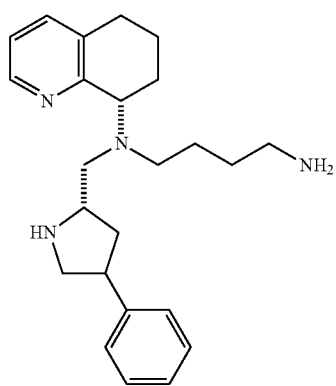 | 379 (M + H⁺) |
| 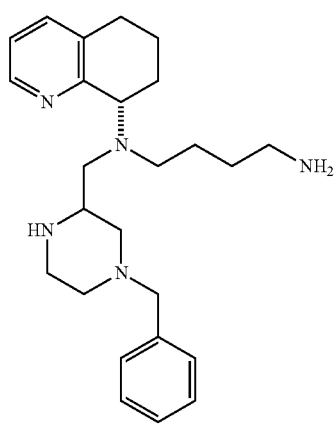 | 408 (M + H⁺) |

| Compound | Mass Spectroscopy Data |
|----------|------------------------|
| | 408 (M + H⁺) |
| | 351 (M + H⁺) |
| | 365 (M + H⁺) |
| | 365 (M + H⁺) |

-continued

| Compound | Mass Spectroscopy Data |
|---|---|
| 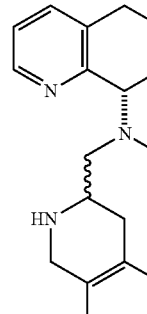 | 308 (M + H⁺) |
| 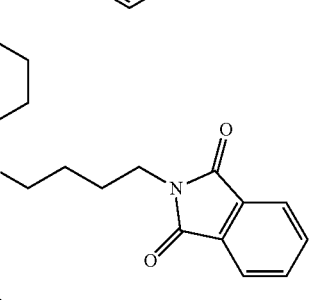 | 495 (M + H⁺) |

Example 2

MAGI-CXCR4 HIV-1 MB Assay Procedure

Cell Preparation—MAGI-CXC4 cells (obtained from the NIH AIDS Research and Reference Reagent Program) are passed into T-75 flasks prior to use in the antiviral assay. MAGI-CXCR4 cells are derived from HeLa-CD4-LTR-β-gal cells. The cells have been engineered to express high levels of CD4 and CCR5 and contain one copy of the HIV-1 LTR promoter driving expression of the β-galactosidase gene upon HIV-1 Tat transactivation. On the day preceding the assay, the cells are plated at $1.0 \times 10^4$ per well and incubated at 37° C. overnight. Total cell and viability quantification is performed using a hemacytometer and trypan blue exclusion. Cell viability is greater than 95% for the cells to be utilized in the assay.

Virus Preparation—The virus used for these tests is the CCR5-tropic virus strain HIV-1$_{IIIB}$ (CXCR4-tropic strain HIV-1$_{NL4-3}$ is also available for use). This virus was obtained from the NIH AIDS Research and Reference Reagent Program and was grown in Ghost Hi5/MAGI-CXCR4 co-cultures for the production of stock virus pools. For each assay, a pre-titered aliquot of virus is removed from the freezer (−80° C.) and allowed to thaw slowly to room temperature in a biological safety cabinet. The virus is re-suspended and diluted into tissue culture medium such that the amount of virus added to each well in a volume of 50 μL is approximately ten TCID$_{50}$/well (~0.001 TCID$_{50}$/cell).

Assay Setup—Compounds are evaluated at one or two concentrations (e.g., for initial screening) or in dose-response at six concentrations (triplicate wells/concentration). On the day of assay setup, compound dilutions are prepared at two-times (2×) the final required concentrations. Media used for plating the cells the day before assay setup is aspirated from the plates and replaced with 50 μL of the 2× compounds, followed by the addition of 50 μL of virus, which dilutes the compounds to the final 1× concentrations. Cell control wells (cells only) and virus control wells (cells plus virus) are included on each assay plate. Identical uninfected assay plates (virus replaced with media) are prepared for parallel cytotoxicity testing. The cultures are incubated for 48 hours or 6 days (depending on compound or client requirements) after which antiviral efficacy is measured as the inhibition of β-galactosidase reporter expression and cytotoxicity is monitored by MTS staining.

A chemiluminescent endpoint is used to determine the extent of β-galactosidase expression as a measure of HIV-1 infection of the cells. Once HIV-1 has attached and entered the MAGI-CXCR4 cells, HIV-1 Tat transactivates the LTR dependent β-galactosidase enzyme to express higher than normal levels of β-galactosidase. Thus there is a direct relationship between the level of HIV-1 infection and the level of β-galactosidase detected in the cells. At 48 hours post infection, plates are aspirated and PBS is added to each well. Gal-screen reagent (Tropix, Bedford, Mass.) is then added per the manufacturer's instructions for chemiluminescent detection of β-galactosidase activity and incubated at room temperature for 90 minutes. The resulting chemiluminescence signal is then read using a Microbeta Trilux luminescence reader (PerkinElmer/Wallac).

At assay termination, the cytotoxicity assay plates are stained with the soluble tetrazolium-based dye MTS (CellTiter Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. The MTS is a stable solution that does not require preparation before use. At termination of the assay, 15 μL of MTS reagent is added per well. The microtiter plates are then incubated 1.5-2 hrs at 37° C.; the incubation interval was chosen based on empirically determined times for optimal dye reduction. The plates are read spectrophotometrically at 490/650 nm with a Molecular Devices Vmax plate reader. Percent inhibition of virus replication and percent cell viability at each concentration are calculated using an in-house computer program.

The results obtained with the assay for the compounds in this disclosure are listed below.

| Compound | MAGI HIV IIIB<br>% Inhibition at 1 uM or IC$_{50}$ |
|---|---|
| [structure] | 0% @ 1 uM |
| [structure] | 0% @ 1 uM |
| [structure] | 0% @ 1 uM |

| Compound | MAGI HIV IIIB % Inhibition at 1 uM or IC$_{50}$ |
|---|---|
| 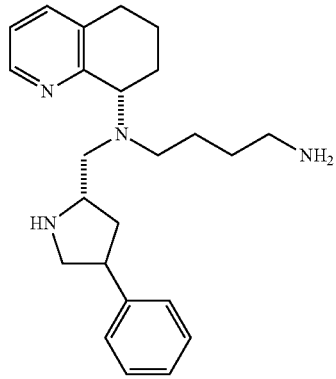 | 20% @ 1 uM |
| 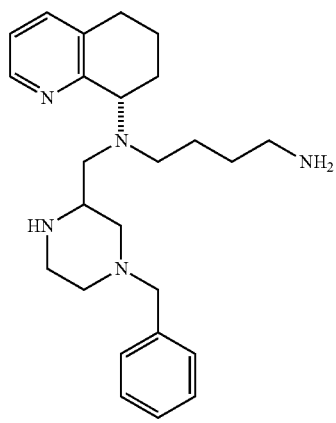 | 30 nM<br>92% @ 1 uM |
| 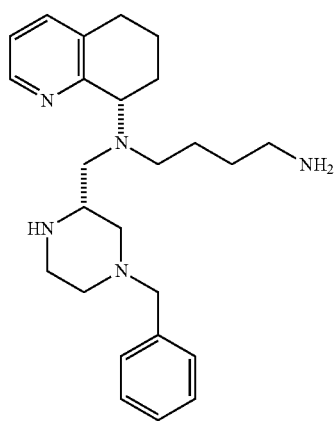 | 150 nM<br>95% @ 1 uM |

| Compound | MAGI HIV IIIB<br>% Inhibition at 1 uM or IC$_{50}$ |
|---|---|
| 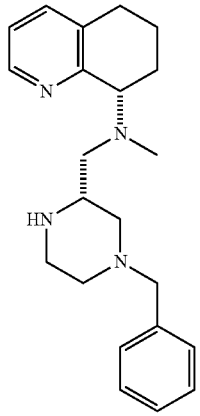 | 41% @ 1 uM |
| 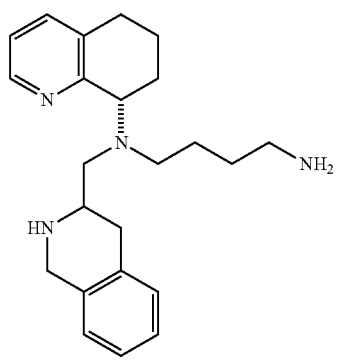 | 5 nM<br>94% @ 1 uM<br>(S-isomer) |
| 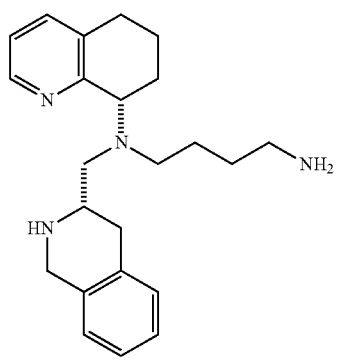 | 60 nM<br>96% @ 1 uM<br>(R-isomer) |

| Compound | MAGI HIV IIIB % Inhibition at 1 uM or IC$_{50}$ |
|---|---|
| *(structure: 5,6,7,8-tetrahydroquinolin-8-yl linked via N to (1,2,3,4-tetrahydroquinolin-2-yl)methyl and 4-aminobutyl)* | 42% @ 1 uM |
| *(structure: similar tetrahydroquinoline/tetrahydroquinoline diamine with 4-aminobutyl)* | 31% @ 1 uM |
| *(structure: 5,6,7,8-tetrahydroquinolin-8-yl-N(Me)-CH$_2$-tetrahydroisoquinoline)* | 30% @ 1 uM |
| *(structure: 5,6,7,8-tetrahydroquinolin-8-yl / tetrahydroisoquinolinyl-methyl amine with N-phthalimidobutyl)* | 25% @ 1 uM |

Further testing to determine inhibitory concentrations and toxicity was performed on compounds 4, 5, 8 and 9 and results reported below. IC$_{50}$ and IC$_{90}$ values are reported, as well as TC$_{50}$ values and therapeutic index. AMD3100 and a CCR5 inhibitor TAK779 are shown as controls.

| Compound | HIV IC$_{50}$ (uM) | HIV IC$_{90}$ (uM) | TC$_{50}$ (uM) | T.I. (TC$_{50}$/IC$_{50}$) |
| --- | --- | --- | --- | --- |
| 9 | 0.03 | 0.44 | >10 | >333 |
| 8 | 0.15 | 0.72 | >10 | >67 |
| 5 | 0.06 | 0.56 | >10 | >5000 |
| 4 | 0.005 | 0.05 | >10 | >170 |
| AMD3100 | 0.002 | 0.007 | >10 | >5000 |
| TAK779 | >10 | >10 | >10 | N/A |

Example 3

Peripheral Blood Mononuclear Cell and sdf-1 Assays

To test efficacy of selected compounds, peripheral mononuclear cell assays are performed. Cells are infected for 6 days with live HIV IIIB virus and PBM cells are run in parallel for cytotoxicity testing, with or without selected agents. Efficacy of compounds as antagonists of the sdf-1 ligand to CXCR4 receptors was determined in $I^{125}$ labeled sdf-1 displacement assays from CXCR4-expressing CEM cells are performed. AMD3100, Maraviroc (a CCR5 antagonist) and AZT (a reverse transcriptase inhibitor) are run as a standard control. Results on compound 4 are reported below.

| Compound | | PBMC-HIV $IC_{50}$ (uM) | PBMC-HIV $IC_{90}$ (uM) | PBMC $TC_{50}$ (uM) | T.I. ($TC_{50}/IC_{50}$) | $I^{125}$Sdsf-1 binding $IC_{50}$ (uM) |
|---|---|---|---|---|---|---|
| 4 | 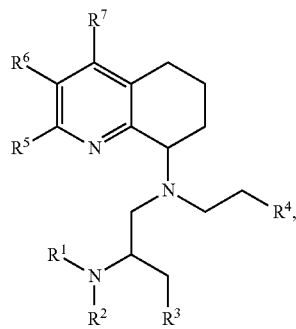 | 0.035 | 0.244 | >10 (47) | >1000 | 0.3 |
| AMD3100 | | 0.032 | 0.134 | >5 | >150 | 0.454 |
| Maraviroc | | >2 | >2 | >2 | N/A | N/A |
| AZT | | 0.004 | 0.07 | >1 | >240 | N/A |

The invention claimed is:

1. A compound comprising formula IB, formula IB or salts thereof wherein, $R^1$ is hydrogen or alkyl, wherein $R^1$ is optionally substituted with one or more, the same or different, $R^{10}$;

$R^2$ and $R^3$ together with the atoms they are bonded to form a carbocyclyl or heterocyclyl, wherein the carbocyclyl or heterocyclyl are optionally substituted with one or more, the same or different, $R^{10}$;

$R^4$ is hydrogen, alkyl, halogen, cyano, hydroxy, amino, mercapto, formyl, carboxy, carbamoyl, alkoxy, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$;

$R^5$, $R^6$ and $R^7$ are each individually and independently hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^1$ is hydrogen.

3. The compound of claim 1, wherein $R^4$ is —CH$_2$CH$_2$NH$_2$ optionally substituted with one or more the same or different $R^{10}$.

4. The compound of claim 1, wherein $R^5$, $R^6$, and $R^7$ are hydrogen, halogen, alkyl, or alkoxy.

5. The compound of claim 1, wherein $R^{13}$ is alkyl, alkoxy, phenyl, benzyl, benzyloxy, benzoyl, optionally substituted with one or more, the same or different, $R^{14}$.

6. The compound of claim 1 selected from:
$N^1$—(((S)-1,2,3,4-tetrahydroisoquinolin-3-yl)methyl)-$N^1$—((S)-5,6,7,8-tetrahydroquinolin-8-yl)butane-1,4-diamine;
$N^1$—(((R)-1,2,3,4-tetrahydroisoquinolin-3-yl)methyl)-$N^1$—((S)-5,6,7,8-tetrahydroquinolin-8-yl)butane-1,4-diamine;
$N^1$—(((S)-4-benzylpiperazin-2-yl)methyl)-$N^1$—((S)-5,6,7,8-tetrahydroquinolin-8-yl)butane-1,4-diamine;
$N^1$—(((R)-4-benzylpiperazin-2-yl)methyl)-$N^1$—((S)-5,6,7,8-tetrahydroquinolin-8-yl)butane-1,4-diamine;
((R)-3-(((4-aminobutyl)((S)-5,6,7,8-tetrahydroquinolin-8-yl)amino)methyl)piperazin-1-yl)(phenyl)methanone;
((S)-3-(((4-aminobutyl)((S)-5,6,7,8-tetrahydroquinolin-8-yl)amino)methyl)piperazin-1-yl)(phenyl)methanone;
$N^1$—(((R)-4-phenylpiperazin-2-yl)methyl)-$N^1$—((S)-5,6,7,8-tetrahydroquinolin-8-yl)butane-1,4-diamine;
$N^1$—(((S)-4-phenylpiperazin-2-yl)methyl)-$N^1$—((S)-5,6,7,8-tetrahydroquinolin-8-yl)butane-1,4-diamine;
$N^1$-(((2S)-4-phenylpiperidin-2-yl)methyl)-$N^1$—((S)-5,6,7,8-tetrahydroquinolin-8-yl)butane-1,4-diamine;
$N^1$-(((2R)-4-phenylpiperidin-2-yl)methyl)-$N^1$—((S)-5,6,7,8-tetrahydroquinolin-8-yl)butane-1,4-diamine;
(2S)-benzyl 4-(4-aminobutoxy)-2-(((4-aminobutyl)((S)-5,6,7,8-tetrahydroquinolin-8-yl)amino)methyl)pyrrolidine-1-carboxylate;
(2R)-benzyl 4-(4-aminobutoxy)-2-(((4-aminobutyl)((S)-5,6,7,8-tetrahydroquinolin-8-yl)amino)methyl)pyrrolidine-1-carboxylate;
$N^1$-(((2S)-4-(benzyloxy)pyrrolidin-2-yl)methyl)-$N^1$—((S)-5,6,7,8-tetrahydroquinolin-8-yl)butane-1,4-diamine;
$N^1$-(((2S)-4-(benzyloxy)pyrrolidin-2-yl)methyl)-$N^1$—((S)-5,6,7,8-tetrahydroquinolin-8-yl)butane-1,4-diamine;
$N^1$-(((2S)-4-phenylpyrrolidin-2-yl)methyl)-$N^1$—((S)-5,6,7,8-tetrahydroquinolin-8-yl)butane-1,4-diamine;
$N^1$-(((2R)-4-phenylpyrrolidin-2-yl)methyl)-$N^1$—((S)-5,6,7,8-tetrahydroquinolin-8-yl)butane-1,4-diamine;
$N^1$—((S)-isoindolin-1-ylmethyl)-$N^1$—((S)-5,6,7,8-tetrahydroquinolin-8-yl)butane-1,4-diamine;
$N^1$—((R)-isoindolin-1-ylmethyl)-$N^1$—((S)-5,6,7,8-tetrahydroquinolin-8-yl)butane-1,4-diamine;
$N^1$—(((S)-1,2,3,4-tetrahydroisoquinolin-1-yl)methyl)-$N^1$—((S)-5,6,7,8-tetrahydroquinolin-8-yl)butane-1,4-diamine;
$N^1$—(((R)-1,2,3,4-tetrahydroisoquinolin-1-yl)methyl)-$N^1$—((S)-5,6,7,8-tetrahydroquinolin-8-yl)butane-1,4-diamine;
$N^1$—(((S)-1,2,3,4-tetrahydroquinolin-2-yl)methyl)-$N^1$—((S)-5,6,7,8-tetrahydroquinolin-8-yl)butane-1,4-diamine; and
$N^1$—(((R)-1,2,3,4-tetrahydroquinolin-2-yl)methyl)-$N^1$—((S)-5,6,7,8-tetrahydroquinolin-8-yl)butane-1,4-diamine.

7. A pharmaceutical comprising a compound as described in claim 1 or salt thereof and a pharmaceutically acceptable excipient, diluent, or carrier.

8. The pharmaceutical composition of claim 7 wherein the compound is in greater than 60% diastereomeric excess, wherein formula I is formula IF, IG, IJ, or IK,

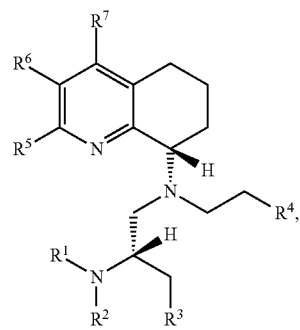
formula IF

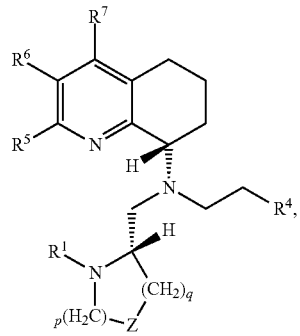
formula IG

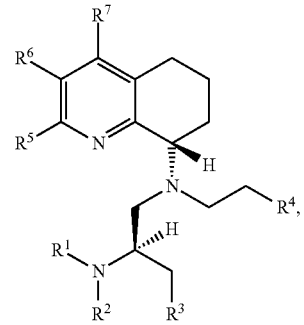
formula IJ

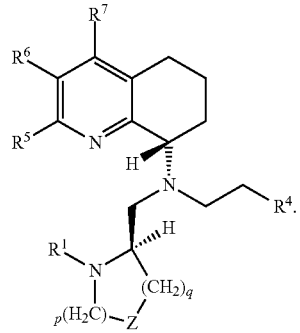
formula IK

9. The pharmaceutical composition of claim 7 further comprising another active ingredient.

10. A method of treating a viral infection comprising administering pharmaceutical composition comprising a compound as described in claim 1 to a subject in need thereof.

11. A method of treating a viral infection comprising administering pharmaceutical composition comprising a compound as described in claim 1 in combination with another active ingredient to a subject in need thereof.

12. The method of claim 10, wherein the viral infection is an HIV infection.

13. A compound of formula IC,

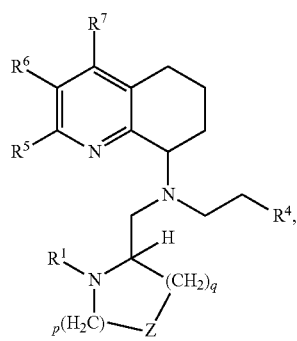
formula IC or salt thereof, wherein
Z is the bridging group —(CH$_2$)$_m$—NR$^{13}$—, —(CH$_2$)$_m$—CHR$^{13}$—, or

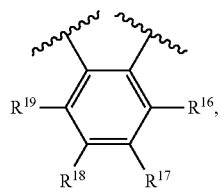

m is 0, 1, or 2;
p is 0, 1, or 2;
q is 0, 1, or 2;
R$^1$ is hydrogen or alkyl, wherein R$^1$ is optionally substituted with one or more, the same or different, R$^{10}$;
R$^4$ is hydrogen, alkyl, halogen, cyano, hydroxy, amino, mercapto, formyl, carboxy, carbamoyl, alkoxy, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^4$ is optionally substituted with one or more, the same or different, R$^{10}$;
R$^5$, R$^6$ and R$^7$ are each individually and independently hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;
R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;
R$^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
R$^{13}$ is hydrogen alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{13}$ is optionally substituted with one or more, the same or different, R$^{14}$;
R$^{14}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{14}$ is optionally substituted with one or more, the same or different, R$^{15}$;
R$^{15}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and
R$^{16}$, R$^{17}$, R$^{18}$ and R$^{19}$ are each individually and independently hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

* * * * *